United States Patent [19]

Yokoyama et al.

[11] Patent Number: 5,461,885
[45] Date of Patent: Oct. 31, 1995

[54] SUBSTRATE FOR RETAINING A HARDENABLE COMPOSITION

[75] Inventors: Genkichi Yokoyama, Hachioji; Takayuki Sekine, Urawa, both of Japan

[73] Assignee: Alcare Co., Ltd., Japan

[21] Appl. No.: 204,812

[22] Filed: Mar. 2, 1994

Related U.S. Application Data

[63] Continuation of Ser. No. 909,795, Jul. 7, 1992, abandoned.

[30] Foreign Application Priority Data

Jul. 8, 1991 [JP] Japan .................................. 3-194853

[51] Int. Cl.$^6$ ..................................................... D04B 1/00
[52] U.S. Cl. ................... 66/170; 66/190; 66/196; 66/202; 602/8; 602/44; 602/76
[58] Field of Search .................... 66/169 R, 190, 66/191, 192, 202, 195, 196, 170; 602/7, 8, 44, 58, 76, 900; 428/253, 290, 423.7, 913

[56] References Cited

U.S. PATENT DOCUMENTS

| | | | |
|---|---|---|---|
| 2,301,426 | 11/1942 | Lovell | 602/7 |
| 2,372,497 | 3/1945 | Johnson et al. | 66/190 |
| 3,881,473 | 5/1975 | Corvi et al. | 66/195 X |
| 4,006,741 | 2/1977 | Arluck | 602/8 |
| 4,427,002 | 1/1984 | Baron et al. | 128/83 |
| 4,502,479 | 3/1985 | Garwood et al. | 128/90 |
| 4,572,171 | 2/1986 | Wegner et al. | 128/90 |
| 4,638,648 | 1/1987 | Gajjar | 66/202 X |
| 4,668,563 | 5/1987 | Buese et al. | 428/230 |
| 4,683,877 | 8/1987 | Ersfield et al. | 602/8 |
| 4,745,912 | 5/1988 | McMurry | 66/202 X |
| 4,785,558 | 11/1988 | Shiomura | 66/196 |
| 4,800,872 | 1/1989 | Buese et al. | 602/8 |
| 4,841,958 | 6/1989 | Ersfield | 602/7 |
| 4,968,542 | 11/1990 | Gasper et al. | 428/423.7 X |
| 5,014,403 | 5/1991 | Buese | 602/8 X |

FOREIGN PATENT DOCUMENTS

| | | |
|---|---|---|
| 0326285 | 1/1989 | European Pat. Off. . |
| 345254 | 7/1980 | Japan . |
| WO8100671 | 7/1980 | WIPO . |

*Primary Examiner*—C. D. Crowder
*Assistant Examiner*—Larry D. Worrell, Jr.
*Attorney, Agent, or Firm*—Haverstock, Garrett & Roberts

[57] ABSTRACT

An improved substrate for retaining a hardenable composition, which substrate utilizes a double face knit having knitting fabrics of multiple bundles formed on both its face and back surfaces, the knitting fabrics being impregnatable with hardenable resin by capillary action and retaining the resin to enable curing thereof into a hard composition, the improved substrate providing the advantages of substrates composed of glass fibers such as strength and good air permeability, while also providing advantages of substrates composed of natural and synthetic fibers such as comfort and non-irritability.

17 Claims, 10 Drawing Sheets

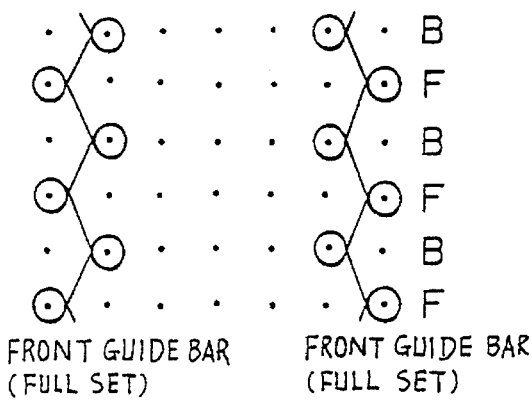
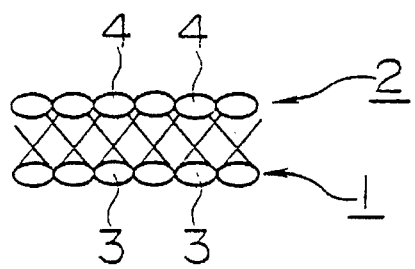
FRONT GUIDE BAR (FULL SET)    FRONT GUIDE BAR (FULL SET)
Fig. 1a
Fig. 1b
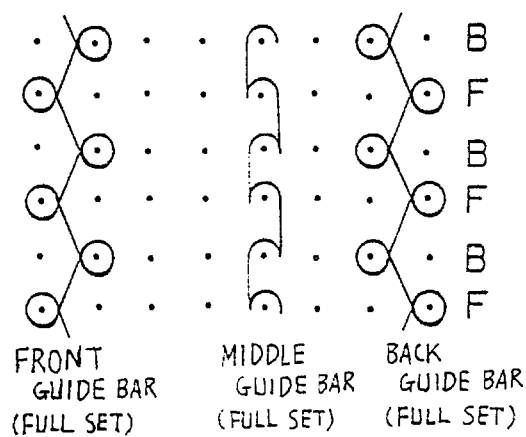
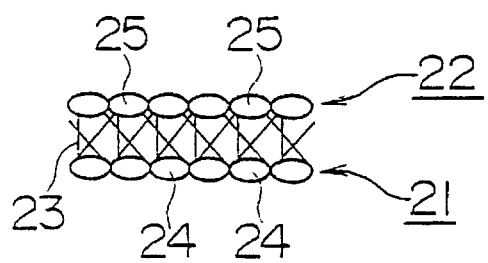
FRONT GUIDE BAR (FULL SET)   MIDDLE GUIDE BAR (FULL SET)   BACK GUIDE BAR (FULL SET)
Fig. 2a
Fig. 2b
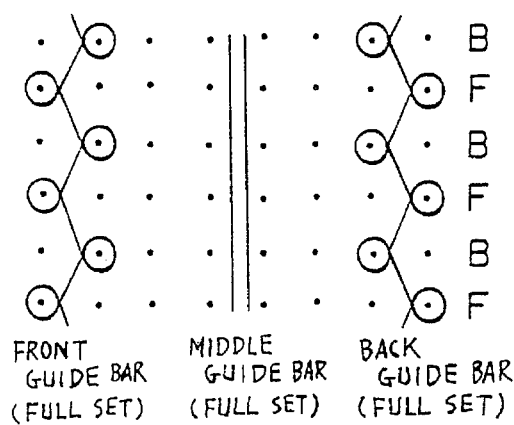
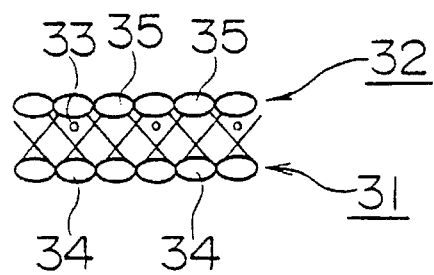
FRONT GUIDE BAR (FULL SET)   MIDDLE GUIDE BAR (FULL SET)   BACK GUIDE BAR (FULL SET)
Fig. 3a
Fig. 3b

FRONT
GUIDE BAR
(FULL SET)

BACK
GUIDE BAR
(FULL SET)

FRONT
GUIDE BAR
(FULL SET)

BACK
GUIDE BAR
(FULL SET)

SUBSTRATE FOR RETAINING A HARDENABLE COMPOSITION

This is a continuation of application Ser. No. 07/909,795 filed on Jul. 7, 1992, now abandoned.

Applicant hereby claims foreign priority benefits under 35 USC §119 of corresponding Japanese Patent Application Serial No. (Hei) 3-194853, filed Jul. 8, 1991.

INDUSTRIAL FIELD OF UTILIZATION

The present invention relates generally to substrates for retaining hardenable compositions for orthopedic and athletic applications, and more particularly to an improved substrate for impregnating and painting with a hardenable composition such as a resin or plaster of Paris and wrapping around or otherwise applying to a portion of the body for fixating, supporting and protecting bone fractures, sprains, dislocations and other injuries and conditions. The present substrate can be embodied as a tape, a sheet or in any other desired form and enables the hardenable composition applied thereto to cure when the substrate is wrapped around or applied to a body portion, providing a light weight, comfortable and non-irritating, yet strong structure for fixating, supporting and protecting the body portion.

BACKGROUND OF THE INVENTION

Prior Art

Known structures or members such as casts and splints for orthopedic and athletic purposes for fixating, supporting and protecting portions of a body generally include hardenable compositions used alone, or alternatively, composites of a hardenable composition applied to a substrate such as a textile, a knit or a porous plastic layer.

Hardenable compositions used alone can include such materials as super linear polyesters such as t-polyisoprene, polycaprolactone, poly 1, 6-hexamethylene azipate, etc; polymer melts such as polyvinyl chloride, polymer alloy, etc; and thermoplastic resins having a low melting point and rigidity at ambient or normal temperatures. Such hardenable compositions are generally provided in sheets or plates having a thickness of about 1–5 mm and when heated can be worked and formed to conform to the shape of a body portion such as a portion of an arm or a leg. Limitations, however, associated with the use of hardenable compositions alone include a relatively heavy weight, a requirement of perforation thereof for the passage of air therethrough, and when overheated, such hardenable compositions alone can stretch and elongate due to their own weight so as to impair modeling or forming of the hardenable composition to a particular body portion. Due to such limitations, the hardenable compositions alone are generally of only limited usefulness.

Hardenable compositions for applying to a substrate such as a fabric, a knit or a porous plastic sheet can include a thermoplastic resin, for instance, a light curable resin that is cured when exposed to a specific wave length of light; or a plaster compound for instance of a gypseous base that is cured when exposed to water; or a water curing urethane resin that contains as its main component a compound having two (2) or more free NCO groups within its molecule such as a urethane prepolymer. Such hardenable compositions can be applied to a tape or sheet of substrate having a coarse mesh texture and composed of such materials as cotton, polyester, polypropylene, glass fibers or carbon fibers. Such substrates are generally formed by knitting high modulus fibers such as glass, polyester, polypropyrene or other fibers into textiles having weave patterns such as a marquisette stitch, an atlas stitch, a denbigh stitch, a plain stitch, a rib stitch, a purl stitch or a plain weave pattern, or by modifying those basic patterns, or by knitting with elastomer yarns or finished yarns as insert yarns or system yarns.

Numerous methods for forming substrates including glass fibers therein as suggested above have been proposed. Such known methods include using high elasticity fibers such as glass fibers combined with elastomer fibers in such a way that the elastomer fibers are introduced lengthwise so as to be stretchable by 40–200% in a longitudinal direction thereby making it possible to improve adaptability of the textile while maintaining the strength of the glass fibers, as disclosed in U.S. Pat. No. 4,668,563. Another known method uses glass fibers having an initial elasticity of at least $0.56 \times 10^6$ kg/cm$^2$ woven into a mesh having from 3–31 openings/cm$^2$, which results in a material which can be hardened to a particular set strength within a short period of time and which retains porosity, as disclosed in PCT Patent No. WO81/00671. Still another method uses a cloth sheet composed of glass fibers which cloth sheet has a plurality of protrusions on one of its surfaces thereby improving the lamination properties thereof, as disclosed in Japanese Unexamined Patent Application Publication No. 3-45254. Although those substrates utilizing glass fibers such as disclosed above gain a requisite strength when hardened, they also suffer from a number of shortcomings, namely, high cost and lack of transparency to X-rays making such glass fiber substrates disadvantageous for radiological diagnosis. Further, when such glass fiber substrates are formed having fluffs of fibers extending therefrom, the fluffs when hardened can become pointed like needles and can prick the skin and also scratch clothing. The edge of hardened substrates can also be irritating to the skin. Still further, when a window through the hardened structure is opened to enable treatment during recovery, or the cast or other structure is removed for remission, cutting wastes can be produced that can irritate the skin and cause dermatitis. In addition, such used or wasted casts are incombustible, such that special treatment is require for disposal thereof.

Numerous methods for using natural and synthetic fibers such as cotton, polyester, polyethylene and the like as substrates have also been proposed. For instance, a raschel fabric of natural or synthetic fibers can be formed with the ratio of the average interval between two adjacent wales against the corresponding interval between two adjacent courses being less than 1 to 5, thereby improving the X-ray transparency and the cross-sectional expandability and strength, as disclosed in U.S. Pat. No. 4,572,171. Another known substrate can be formed from nonelastic fibers, or fibers of a low elasticity, with elastic fibers introduced lengthwise, thereby providing the substrate with proper adaptability, sufficient rigidity, low fragility and sufficient durability, as disclosed in EP 0326285A2. Sill another substrate can be formed from less water-absorbing yarns of 400–1500 denier woven into a textile substrate with openings each of about 0.15 to 0.25 square inch, so that such substrate is strong, can be thinly coated with hardenable composition, and can have a good air permeability and X-ray transparency, as disclosed in U.S. Pat. No. 4,427,002. However, an important limitation of substrates of natural or synthetic fibers such as cotton, polyester, polyethylene or the like is weakness making it necessary to use multiple layers of such substrate. Using multiple layers for more strength requires more time for forming or wrapping a cast or other structure and the hardened material is thick so as to be more uncomfortable and burdensome for the wearer and such thickness can impair the air permeability of the structure.

SUMMARY OF THE INVENTION

Means of Solving the Problem

In order to overcome the shortcomings and limitations of known substrates for retaining hardenable materials, the present invention relates to a substrate which can comprise a double layered knit fabric material formed of two knitted webs, one web forming the front (face) surface of the substrate while the other web forms the back surface of the substrate, the knitted webs being knitted using yarns comprising multiple fiber bundles with a knitting machine having two or more needle bars.

It is preferred to provide a substrate construction wherein the loops forming the knitted webs of both the face and back surfaces of the double layered knit material are overlaid in opposed relationship one upon the other. The yarn composed of fiber bundles can include spinning yarns of natural fibers such as cotton, staple fiber, and others, or alternatively multifilament fibers composed of multiple bundles of synthetic filaments such as polyester, polyethylene, polypropylene, polyamid, polyvinylidene chloride, or the like. It is also desirable to select a combination of a yarn and a hardenable composition which prevents a curing agent for the hardenable composition from curing during storage in accordance with physical and chemical properties of the hardenable composition. For example, for use with a hardenable composition such as a plaster compound which hardens through hydrating reaction, natural fibers can be used. For use with a resin that hardens through reaction with light or water, synthetic fibers can be used. For use with commonly used curing resins containing urethane polymer as a main component, it is advantageous to employ yarns of polyester fibers.

As a knitting machine for making the present substrate, warp, weft or circular knitting machines having two or more needle bars and capable of forming a bilayered fabric can be used.

Operation of the Invention

When a hardenable composition is applied to a substrate constructed according to the teachings of the present invention, the hardenable composition readily penetrates through the yarns of the substrate by way of a capillary action, the hardenable composition thereby impregnating into the substrate. Once impregnated into the substrate, the hardenable composition is resistive to removal by the same mechanism. Further, the surface area of the yarn is several times greater than that of the individual filaments thereof, such that a suitable amount of the hardenable composition can be adequately retained by the yarn, and when the hardenable composition is cured the assembly has a structure similar in construction to, but much smaller than the reinforcing structures or skeletons used in making reinforced concrete.

Still further, by overlaying the loops forming the respective front (face) and back knitting fabric layers or webs one upon the other, the thickness per layer of the knit can become greater so as to be stronger and provide a desired fixating force with relatively few wraps or rolls of the substrate fabric.

Still further, by providing a space interposed between the front (face) and back knitting fabric layers or webs, a structure similar to a honeycomb configuration can be obtained which allows the assembly to be light as well as strong.

It is therefore a principle object of the present invention to provide a substrate for retaining a hardenable composition which is as strong and as air permeable as known substrates composed of glass fibers.

Another object is to provide a substrate which is as easy to use as a substrate composed of conventional natural or synthetic fibers.

Another object is to provide a substrate which is soft to the skin of a wearer, can be easily cut to a desired form and the cut ends thereof being non-irritating to the skin.

Another object is to provide a substrate which does not require any special treatment for its disposal, has a smooth cured surface when finished and does not have a tendency to curl when processed or rolled.

These and other objects and advantages of the present invention will become apparent to those skilled in the art after considering the following detailed specification in conjunction with the accompanying drawings.

BRIEF DESCRIPTION OF THE DRAWINGS

FIG. 1a is a system diagram showing the relationship of the needle bars and guide bars of a knitting machine for producing a preferred embodiment of a substrate according to the present invention, and FIG. 1b is a cross-sectional schematic view of the substrate knitted according to the system diagram of FIG. 1a;

FIG. 2a is a system diagram showing the relationship of the needle bars and guide bars of a knitting machine for producing an alternative embodiment of a substrate according to the present invention, and FIG. 2b is a cross-sectional schematic view of a substrate knitted according to the system diagram of FIG. 2a;

FIG. 3a is a system diagram for producing another alternative substrate embodiment, and FIG. 3b is a cross-sectional schematic view of a substrate knitted according to the system diagram of FIG. 3a;

FIGS. 4b, 4c and 4d are each partial cross-sectional schematic views of designated portions of a substrate knitted according to the system diagram of FIG. 4a;

FIG. 5b is a cross-sectional schematic view of a substrate knitted according to the system diagram of FIG. 5a;

FIGS. 6b, 6c, 6d, 6e and 6f are each partial cross-sectional schematic views of designated portions of a substrate knitted according to the system diagram of FIG. 6a;

FIG. 7b is a cross-sectional schematic view of a substrate knitted according to the system diagram of FIG. 7a;

FIG. 8b is a cross-sectional schematic view of a substrate knitted according to the system diagram of FIG. 8a;

FIG. 9b is a cross-sectional schematic view of a substrate knitted according to the system diagram of FIG. 9a;

FIG. 10b is a cross-sectional schematic view of a substrate knitted according to the system diagram of FIG. 10a;

FIG. 11b is a cross-sectional schematic view of a substrate knitted according to the system diagram of FIG. 11a;

DETAILED DESCRIPTION OF THE PREFERRED EMBODIMENTS

Figure 4A:
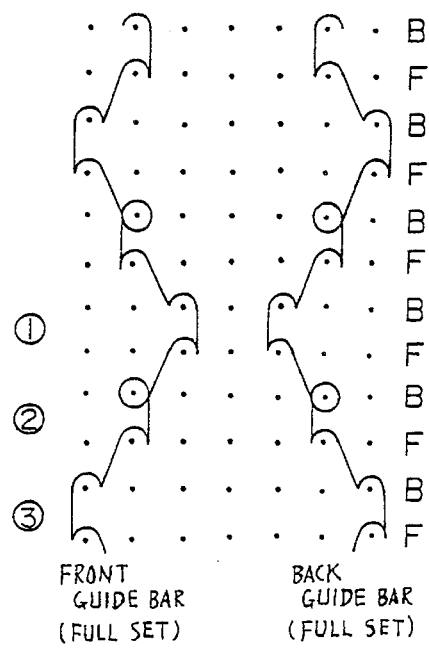
FIG. 4a is a system diagram for producing another alternative substrate embodiment.

Embodiments of the present substrate will now be described in reference to the drawings. In particular, Embodiments 1–6 are each substrates produced with a warp knitting machine, and Embodiments 7 and 8 are each substrates produced with a weft knitting machine. To enable comparing the above embodiments to substrates constructed by conventional methods, substrates that were manufactured with a conventional warp knitting machine are described in Comparative Examples 1 and 2 and substrates manufactured with a conventional weft knitting machine are described in Comparative Example 3.

Evaluated properties of the respective substrates are as follows. A test piece of each substrate approximately 5 cm wide was loaded with a weight of approximately 1 kg and the stretch of the substrate measured to obtain the elongation thereof. A urethane prepolymer water-curable resin composition was then applied to each substrate. Excess resin was removed by squeezing the substrate through a roller to produce a test piece or sample of substrate of approximately 5 cm wide. Each test piece was then wound three times around a pipe of 60 mm diameter and the pipe removed leaving a cylinder of resin impregnated substrate. The cylinder was allowed to cure for twenty-four hours and was compressed diametrically, the compressive stress thereof being measured when the distortion was at 5 mm. The cylinder strength was then calculated. The amount of the resin applied during preparation of the test piece was also measured to enable calculating the maximum retention of the resin in the substrate.

Embodiment 1

Using two yarns of 250 denier comprising 48 bundles of filaments (250d/48F) of polyester as the front yarn and two yarns of 250d/48F of polyester as the back yarn, a double layered knit was knitted as illustrated in the system diagram of FIG. 1a. The letter F in FIG. 1a represents the front needle bar and the letter B represents the back needle bar. This substrate had 19 warps/inch and 12 wefts/inch as its density, weighed 321 g/m$^2$, had an elongation of 17%, had a resin retention of 353 g/m$^2$, and its cylinder strength was 16.78 kg. FIG. 1b is a schematic diagram illustrating the interrelationship of needle loops and sinker loops in the cross-section of the substrate wherein the numeral 1 represents the front or face knitted web or fabric, the numeral 2 represents the back knitted web or fabric and the loops 3 and 4 overlap each other.

Embodiment 2

A modified knit was produced by combining the knitting system as shown in Embodiment 1 with a chain stitch as follows. Polyester yarn of 150d/24F was used as the front yarn, polyester yarn of 150d/24F was used as the back yarn and polyester wooly-finished yarn of 150d was used as the middle yarn for the chain stitch. The respective yarns were knitted into a double layered knit corresponding to a system diagram as shown in FIG. 2a. The letter F in FIG. 2a represents the front needle bar and the letter B represents the back needle bar. This substrate had 20 warps/inch and 14 wefts/inch as its density, weighted 319 g/m$^2$, had an elongation of 35%, a resin retention of 310 g/m$^2$ and its cylinder strength was 18.50 kg. FIG. 2b is a schematic diagram illustrating the interrelationship of needle loops and sinker loops in the cross-section of the substrate of Embodiment 2 wherein the numeral 21 represents the front or face knitted web or fabric, numeral 22 represents the back knitted web or fabric and numeral 23 represents the yarn of the chain stitch and the loops 24 and 25 of the knitted fabrics 21 and 22 overlap each other.

Embodiment 3

A modified knitting was achieved by combining the knitting system as shown in Embodiment 1 with expansion yarns introduced in the warp direction to gain expandability. Polyester yarns of 150d/24F were used as the front yarn, polyester yarns of 150d/24F were used as the back yarn and polyester finished yarns of 75d were used as the middle yarn, which respective yarns were knitted into a double layered knit having a system diagram as shown in FIG. 3a. The letter F in FIG. 3a represents the front needle bar and the letter B represents the back needle bar. This substrate had 20 warps/inch and 15 wefts/inch as its density, weighed 268 g/m$^2$, had an elongation of 47%, a resin retention of 294 g/m$^2$ and its cylinder strength was 7.34 kg. FIG. 3b is a schematic diagram illustrating the interrelationship of needle loops and sinker loops in the cross-section of the substrate wherein the numeral 31 represents the front or face knitted web or fabric, the numeral 32 represents the back knitted web or fabric and the numeral 33 represents the middle yarn and the loops 34 and 35 of the knitted fabrics 31 and 32 overlap each other.

Embodiment 4

Figure 4B:
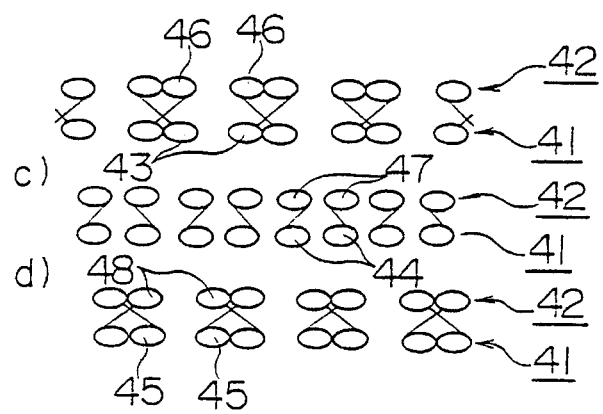

Polyester yarns of 250d/48F were used as the front yarn and polyester yarns of 250d/48F were used as the back yarn and were knitted into a double face knit having a system diagram as shown in FIG. 4a. The letter F in FIG. 4a represents the front needle bar while the letter B represents the back needle bar. This substrate had 14 warps/inch and 15 wefts/inch as its density, weighed 295 g/m$^2$, had an elongation of 22%, a resin retention of 305 g/m$^2$ and its cylinder strength was 11.30 kg. FIGS. 4b, 4c and 4d are each partial cross-sectional schematic diagrams illustrating the interrelationship of needle loops and sinker loops in the areas of the cross-section designated by the numbers ①, ② and ③ of FIG. 4a, wherein the numeral 41 represents the front or face knitted web or fabric, numeral 42 represents the back knitted web or fabric with the loops 43, 44 and 45 of the front fabric 41 and the loops 46, 47 and 48 of the back fabric 42 overlapping each other.

Embodiment 5

Figure 5A:
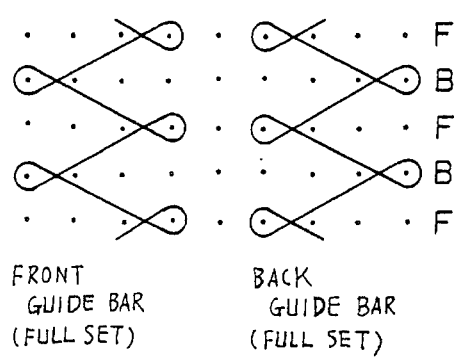
FIG. 5a is a system diagram for producing another alternative embodiment of a substrate according to the present invention.
Figure 5B:
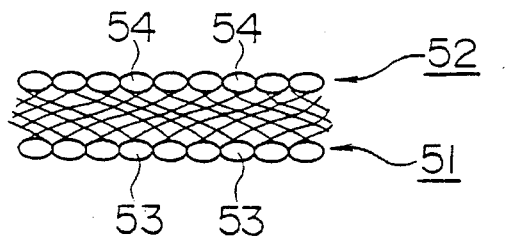

Polyester yarns of 250d/48F were used as the front yarn and polyester yarns of 250d/48F were used as the back yarn and were knitted into a double face knit having system diagram as shown in FIG. 5a. The letter F in FIG. 5a represents the front needle bar while the letter B represents the back needle bar. This substrate had 15 warps/inch and 22 wefts/inch as its finished density, weighed 311 g/m$^2$, had an elongation of 18%, a resin retention of 313 g/m$^2$ and its cylinder strength was 7.84 kg. FIG. 5b is a schematic diagram illustrating the interrelationship of needle loops and sinker loops in the cross-section of this substrate wherein the numeral 51 represents the front or face knitted web or fabric and the numeral 52 represents the back knitted web or fabric with the loops 53 of the front and the loops 54 of the back overlapping each other.

Embodiment 6

Figure 6A:
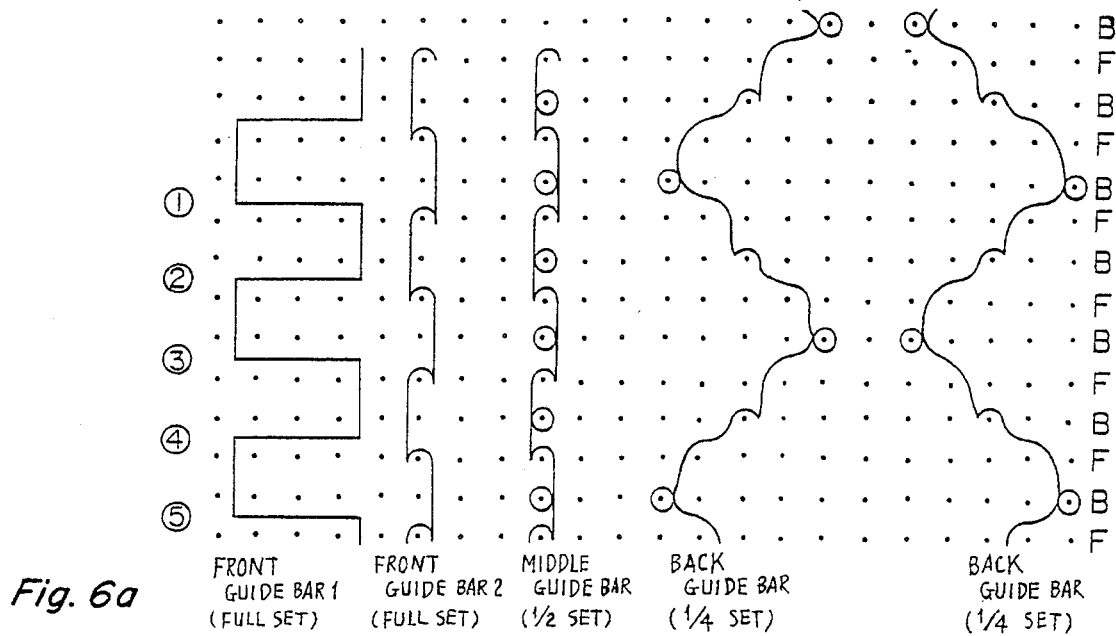
FIG. 6a is a system diagram for producing yet another alternative embodiment of the present substrate.
Figure 6B:
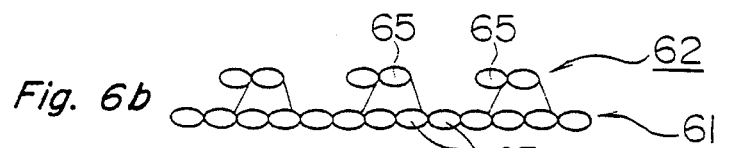
Figure 6C:
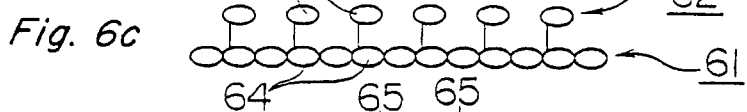
Figure 6D:
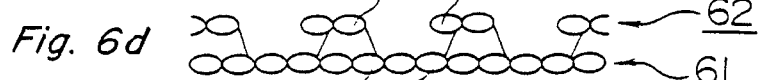
Figure 6E:
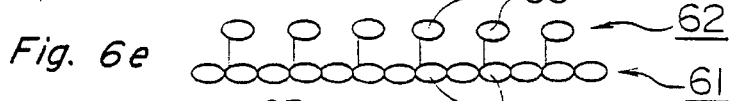
Figure 6F:
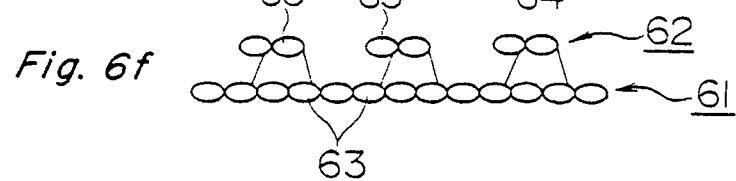

Using double layered knitting with mesh on one side, different knitting systems for both sides and a space between both sides that is occupied by a network connecting the two layers, a substrate can be knitted having a system diagram as shown in FIG. 6a. Hard twist finished yarns of polyester of 250d/24F were used as the front yarn and were knitted into a Marquisette hard twist. Finished yarns of polyester of 250d/24F were used as the back yarn and were knitted into an Atlas knit pattern. The front and back knitted fabrics were bonded by polyester yarns of 250F/24F as the middle yarn. The letter F in FIG. 6a represents the front needle bar while the letter B represents the back needle bar. This substrate weighed 363 g/m$^2$ had an elongation of 35% a resin retention of 410 g/m$^2$ and its cylinder strength was 25.16 kg. FIGS. 6b, 6c, 6d, 6e and 6f are schematic diagrams illustrating the interrelationship of needle loops and sinker loops at the cross-sections numbered ① through ⑤, respectively, wherein the numeral 61 represents the front or face knitted web or fabric and the numeral 62 represents the back knitted web or fabric, with the front fabric having a plain pattern and the back fabric a mesh pattern. Each loop of the back knitted web or fabric is laid over one or more of the loops of the front knitted web or fabric. For example, the loop 65 of the back fabric 62 is laid partly over the two adjacent loops of the front fabric 61 while the loop 66 of the back fabric 62 is laid over one loop, for instance loop 64 of the front fabric 61.

Embodiment 7

Figure 7A:
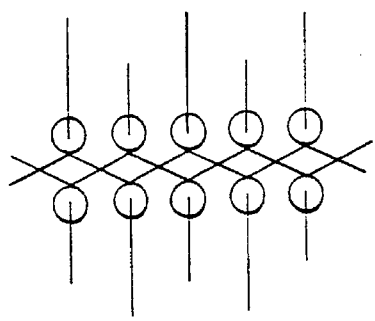
FIG. 7a is a system diagram for producing another alternative embodiment of a substrate according to the present invention.
Figure 7B:
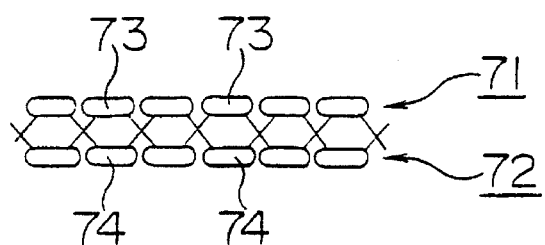

Using smooth knitting polyester yarn of 150d/24F for both layers, a substrate was knitted having a system diagram as shown in FIG. 7a. This substrate had 18 warps/inch and 17 wefts/inch, its finished density was 300 g/m$^2$, the substrate had an elongation of 43%, a resin retention of 280 g/m$^2$ and its cylinder strength was 2.98 kg. FIG. 7b is a schematic diagram illustrating the interrelationship of needle loops and sinker loops at the cross-section of this substrate wherein the numeral 71 represents the front or face knitted web or fabric and the numeral 72 represents the back knitted web or fabric with the loops 73 and 74 of the front and back knitted fabrics 71 and 72 overlapping each other. In this case, both knitted fabric layers are symmetrical.

Embodiment 8

Figure 8A:
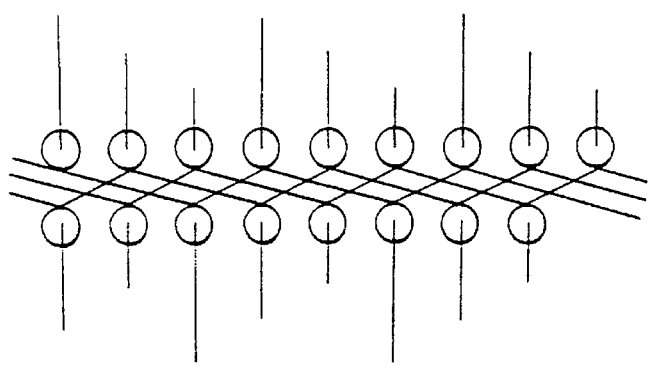
FIG. 8a is a system diagram for producing another alternative embodiment of a substrate according to the present invention.
Figure 8B:
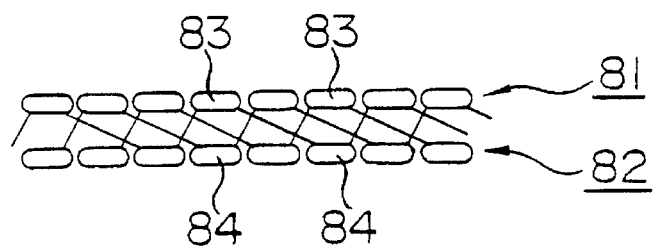

Using a three-stage double layered knitting polyester yarn of 150d/24F for both layers, a substrate was knitted according to the system diagram shown in FIG. 8a. This substrate had 20 warps/inch and 19 wefts/inch, a finished density of 324 g/m$^2$, an elongation of 43%, a maximum resin retention of 301 g/m$^2$ and its cylinder strength was 3.51 kg. FIG. 8b is a diagram illustrating the interrelationship of needle loops and sinker loops at the cross-section of this substrate wherein the numeral 81 represents the front or face knitted web or fabric and the numeral 82 represents the back knitted web or fabric with the space between the two fabric layers made slightly larger than in Embodiment 7. The loops 83 and 84 of the fabrics 81 and 82 overlap each other. In this embodiment also, the two knitted fabric layers or webs are disposed symmetrically.

Comparative Example 1

Figure 9A:
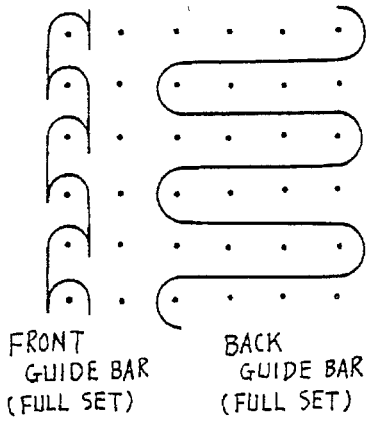
FIG. 9a is a system diagram for producing another alternative embodiment of a substrate according to the present invention.
Figure 9B:
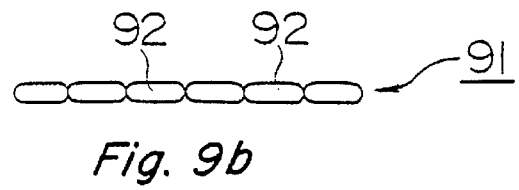

Glass fibers of ECG75 1/0 as the front yarn and glass fibers of ECG75 1/0 as the back yarn were knitted into a fabric having a system diagram as shown in FIG. 9a. This substrate had 14 warps/inch and 14 wefts/inch, a finished density of 320 g/m$^2$, an elongation of 21%, a resin retention of 200 g/m$^2$ and its cylinder strength was 4.50 kg. FIG. 9b is a schematic diagram illustrating the interrelationship of adjacent loops at the cross-section of this substrate wherein the numeral 91 represents a knitted fabric composed of a single layer and the individual loops 92 exist independently with no overlapping of each other.

Comparative Example 2

Figure 10A:
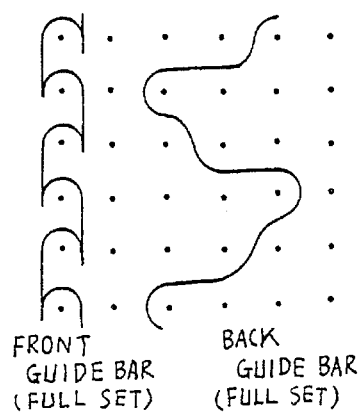
FIG. 10a is a system diagram for producing another alternative embodiment of a substrate according to the present invention.
Figure 10B:
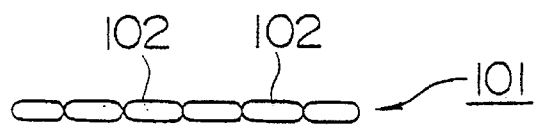

Two hard twisted finished yarns of polyester 150d/48F as the front yarn and four polyester yarns 250d/24F as the back yarn were knitted into a knit having a system diagram as shown in FIG. 10a. This substrate had 9 warps/inch and 8.5 wefts/inch, a finished density of 197 g/m$^2$, an elongation of 67% a resin retention of 250 g/m$^2$ and its cylinder strength was 2.70 kg. FIG. 10b is a schematic diagram illustrating the interrelationship of adjacent loops at the cross-section of this substrate wherein the numeral 101 represents a knitted fabric composed of a single layer and the individual loops 102 exist independently with no overlapping of each other.

Comparative Example 3

Figure 11A:
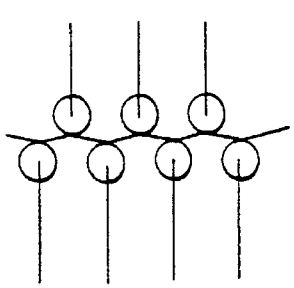
FIG. 11a is a system diagram for producing another alternative embodiment of a substrate according to the present invention.
Figure 11B:
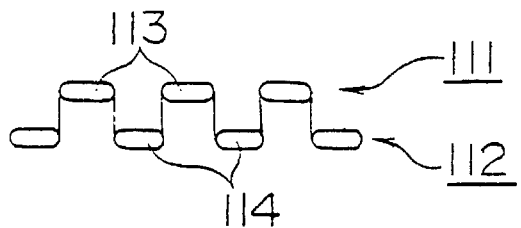

Polyester yarn of 250d/48F was knitted into a knit having a system diagram as shown in FIG. 11a. This substrate had 20 warps/inch and 17 wefts/inch, a finished density of 276 g/m$^2$, an elongation of 38%, a resin retention of 289 g/m$^2$ and its cylinder strength was 1.24 kg. FIG. 11b is a schematic diagram illustrating the interrelationship of adjacent loops at the cross-section of this substrate wherein the numeral 111 represents the front or face knitted web or fabric and the numeral 112 represents the back knitted web or fabric with the loops 113 and 114 of the front and back knitted fabrics 111 and 112 not overlapping each other.

Figure 12A:
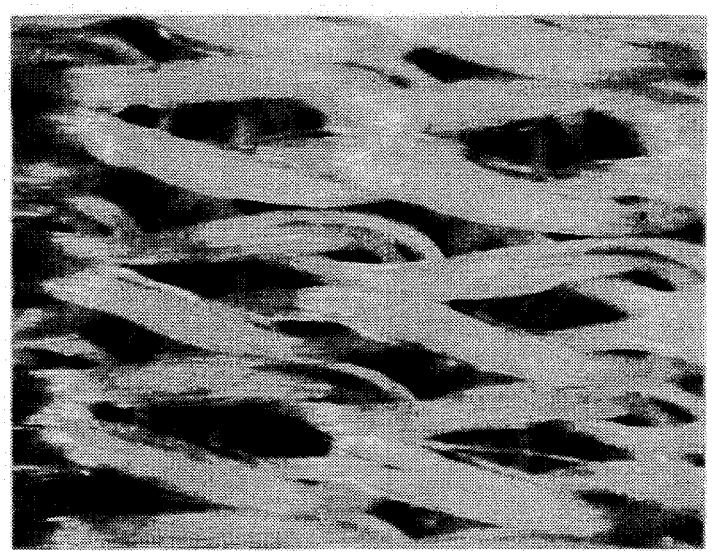
FIGS. 12a, 12b, 12c, 12d and 12e are each photomicrographs of an actual substrate according to FIGS. 1a and 1b.
Figure 12B:
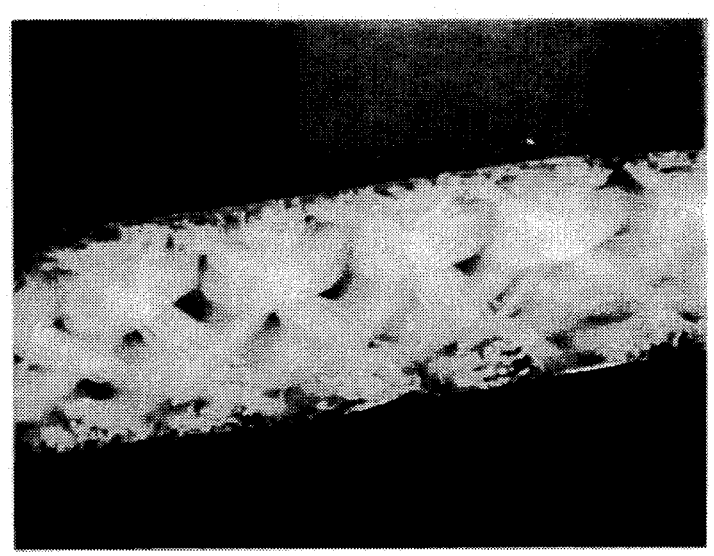
Figure 12C:
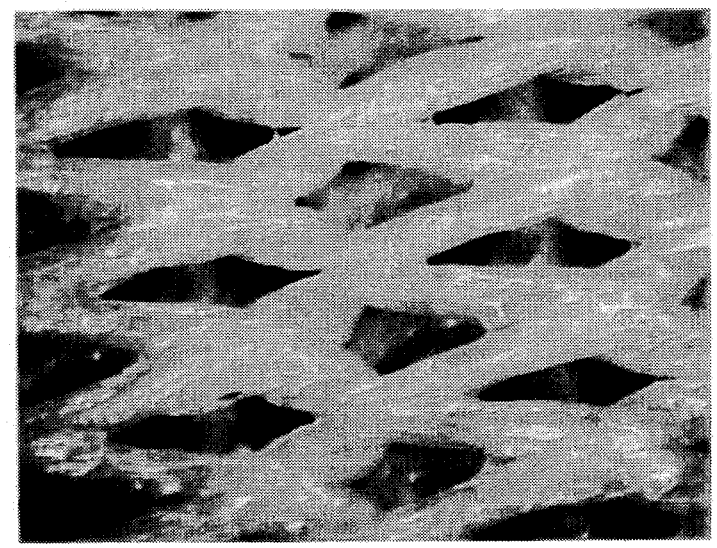
Figure 12D:
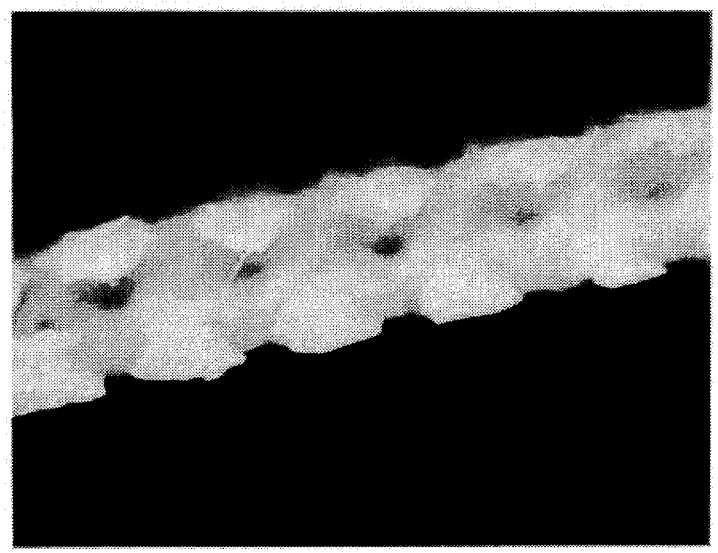
Figure 12E:
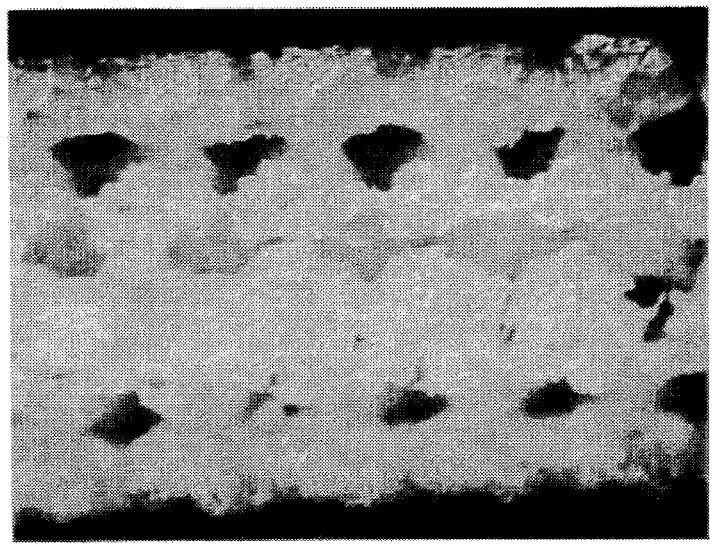

FIGS. 12a, 12b, 12c, 12d and 12e are each photomicrographs of an actual substrate according to Embodiment 1. More particularly, FIG. 12a is a plan view showing the substrate surface; FIG. 12b is a cross-section of the substrate; FIG. 12c is a plan view of the substrate surface after it has been hardened with resin impregnated therein; FIG. 12d is a cross-sectional view of the resin impregnated substrate; and FIG. 12e is a cross-sectional view of a substrate having a three layer structure and hardened with resin impregnated therein.

Figure 13A:
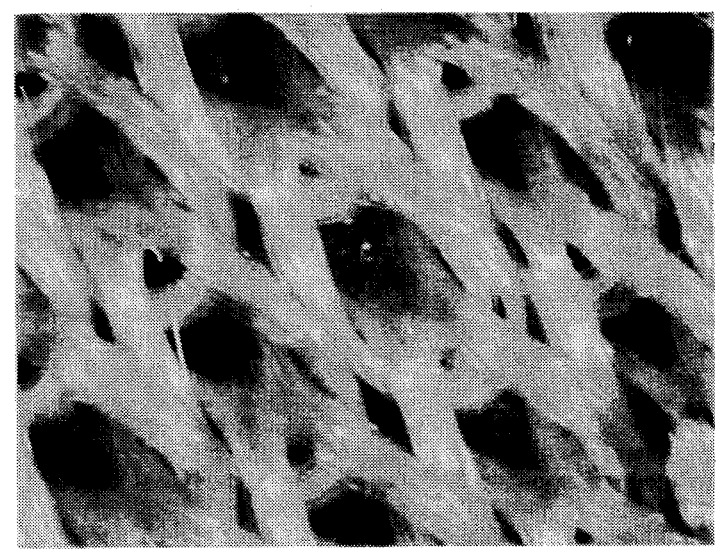
FIGS. 13a, 13b, 13c, 13d and 13e are each photomicrographs of an actual substrate according to FIGS. 3a and 3b.
Figure 13B:
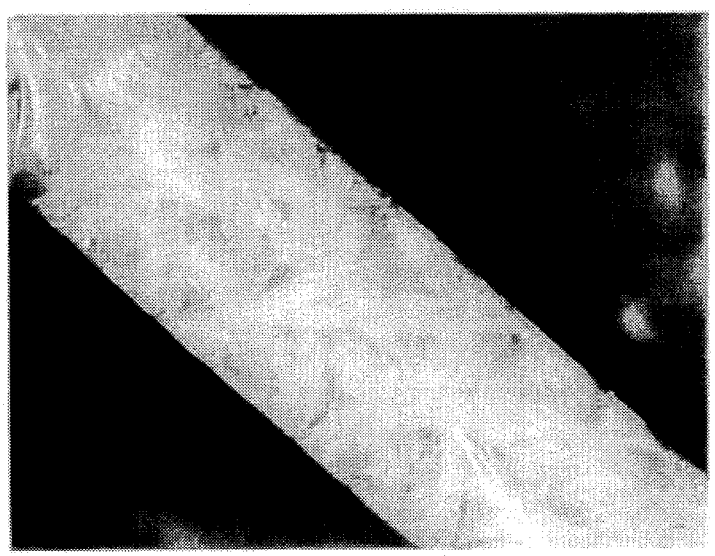
Figure 13C:
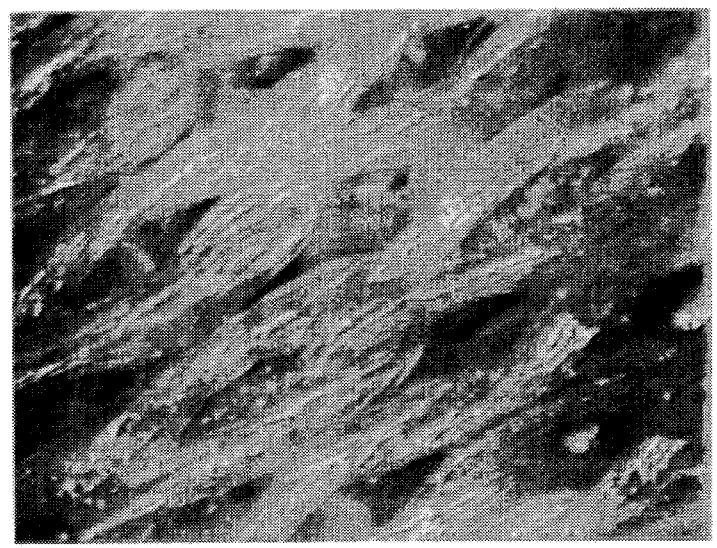
Figure 13D:
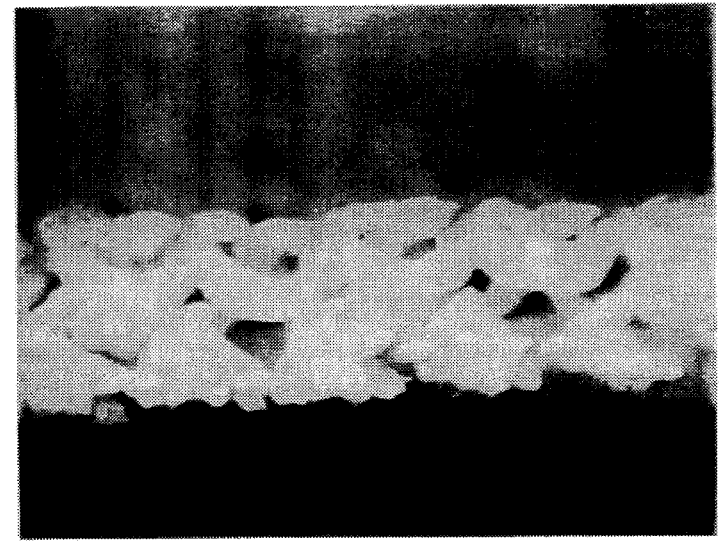
Figure 13E:
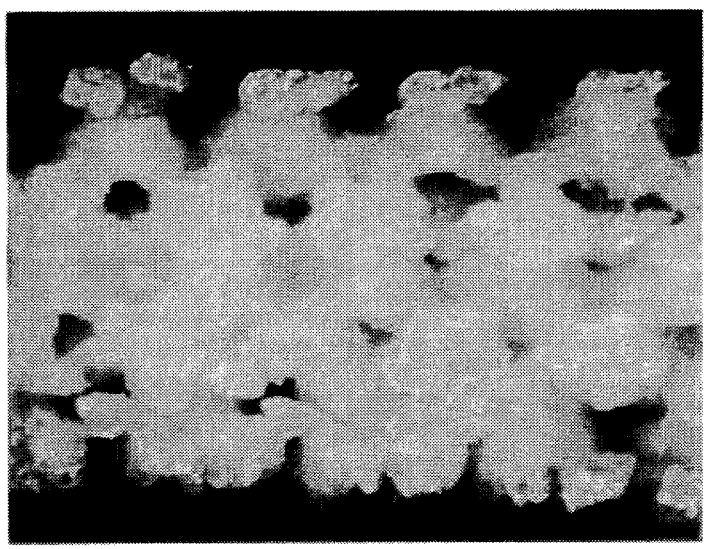

FIGS. 13a, 13b, 13c, 13d and 13e are each photomicrographs of a substrate according to Embodiment 3. More particularly, FIG. 13a is a plan view of the substrate surface; FIG. 13b is a cross-sectional view of the substrate; FIG. 13c is a plan view of the substrate surface hardened with resin impregnated therein; FIG. 13d is a cross-sectional view of the resin impregnated substrate; and FIG. 13e is a cross-sectional view of a substrate having a three layer structure and hardened with resin impregnated therein.

Figure 14A:
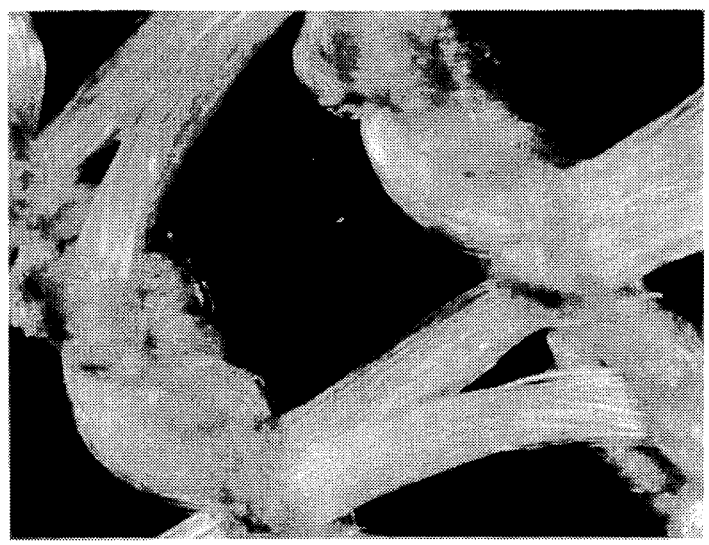
FIGS. 14a, 14b, 14c, 14d and 14e are each photomicrographs of an actual substrate according to Comparative Example 2.
Figure 14B:
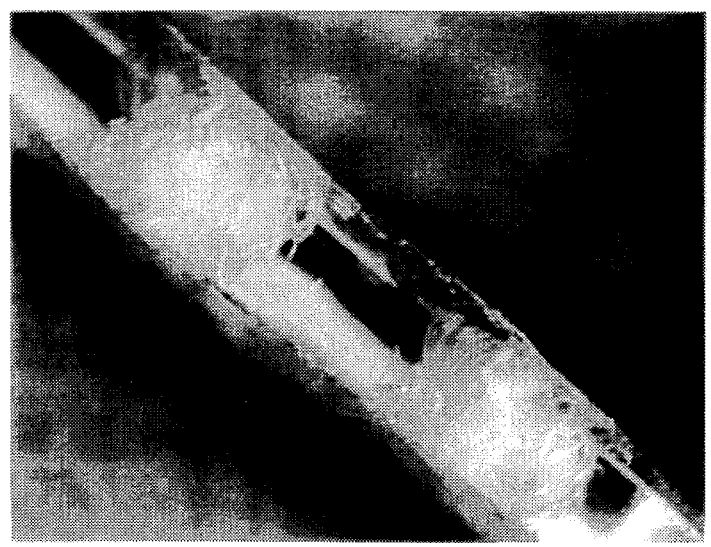
Figure 14C:
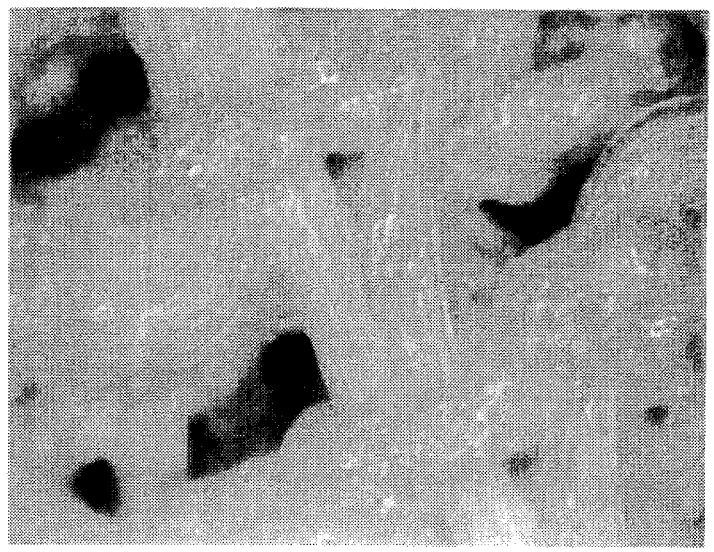
Figure 14D:
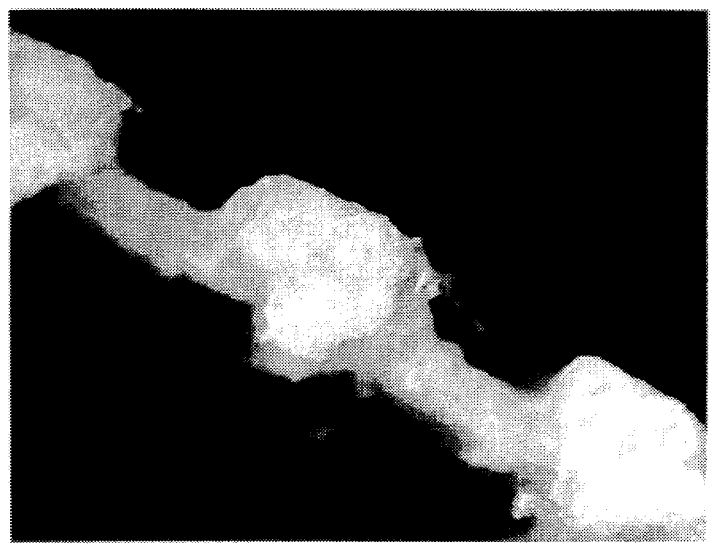
Figure 14E:
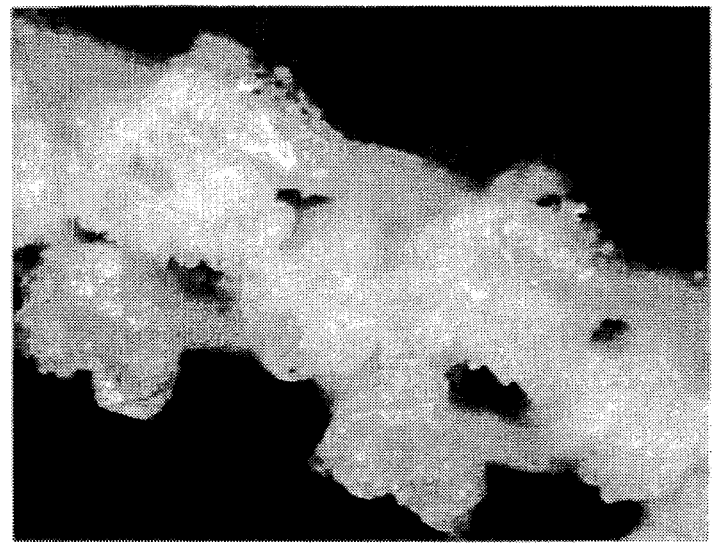

FIGS. 14a, 14b, 14c, 14d and 14e are each photomicrographs of a substrate according to Comparative Example 2. More particularly, FIG. 14a is a plan view of the substrate surface; FIG. 14b is a cross-sectional view thereof; FIG. 14c is a plan view of the substrate surface after it has been hardened with resin impregnated therein; FIG. 14d is a cross-sectional view of the resin impregnated substrate; and FIG. 14e is a cross-sectional view of a substrate of a three layer structure hardened with resin impregnated therein.

As is evident from a comparison between the substrates of Embodiments 1 through 8 of the present invention and Comparative Examples 1 through 3, the substrates according to the present invention provide a sufficiently large retention of resin and have a strength which is at least equal to the strength of the conventional substrates according to Comparative Examples 1 through 3 which contain glass fibers. Comparison of the present embodiments with the comparative examples also shows that greater strength and elongation can be achieved through the proper selection of knitting systems and yarns.

The curing resins usable with the present invention can be classified in three categories according to the form the resin takes when applied to the substrate. The first category is the hydration type resin wherein finely powdered curing resin is dispersed in water, alcohol, vinyl acetate, or a surfacant. In emulsion form the resin is applied to the substrate and dried to allow only the solid component to be retained on the substrate. The second category of resin is the thermoplastic type wherein curing resin dissolved in an organic solvent is applied as a solution to the substrate or is heated until it becomes liquid and is applied as a liquid to the substrate cooled to a normal or ambient temperature so as to be retained therein. The third category of resin is the water-curable or light-curable type wherein the resin has a low viscosity and is directly applied to the substrate. In the present invention, any curing resin regardless of its type can readily penetrate into the substrate through capillary action when it is applied to the substrate surface because the yarns of the fabric consist of multiple fiber bundles. Once the resin is impregnated into the knitting fabric it adheres so strongly to the knitting fabric that its removal therefrom is difficult and a large amount of resin can be retained within the substrate because there the surface area of the yarns is relatively large.

According to the present invention, it is possible to obtain a light and relatively strong curing product that provides a strength at least equal to a conventional product including glass fibers, importantly, without the present invention requiring the use of the glass fibers and with only a few layers of substrate. The present invention also eliminates skin irritation caused by cutting wastes and caused by the edge of the substrate and also eliminates scratching of clothing. The present invention furthermore allows adequate air passage and still retains advantages possessed by conventional substrates of synthetic and natural fibers.

Thus, there has been shown and described several embodiments of a novel substrate for retaining a hardenable composition, which constructions fulfill all of the objects and advantages sought therefor. Many changes, modifications, variations, and other uses and applications of the present construction will, however, become apparent to those skilled in the art after considering this specification and the accompanying drawings. All such changes, modifications, variations, and other uses and applications which do not depart from the spirit and scope of the invention are deemed to be covered by the invention which is limited only by the claims which follow.

What is claimed is:

1. A substrate for retaining a hardenable composition comprising a double layered knit fabric formed of two overlaying knitted webs, each of said knitted webs being knitted with multiple fiber yarns forming a plurality of loops, the loops of one of the webs overlaying the loops of the other web, said loops forming a plurality of spaces between said webs, and yarns extending between said webs connecting each of said loops of said one web to at least one loop of said other web such that said two knitted webs are interlocked with each other continuously throughout said fabric, a hardenable composition applied to said substrate being able to penetrate throughout said substrate by capillarity along said yarns.

2. A substrate for retaining a hardenable composition comprising a double layered knit fabric formed of two overlaying knitted webs, each of said knitted webs being knitted from multiple fiber yarns forming a plurality of loops, each of the loops of one web overlaying at least one of the loops of the other web, said loops forming a plurality of spaces between said webs, and means interlocking each loop of yarn of said one web with at least one loop of yarn of said other web, said means including yarns extending between the loops of yarn of the respective webs, the multiple fiber construction of said yarns enabling a hardenable composition to penetrate throughout said double layered knit fabric by capillarity along the fibers of said yarns.

3. The substrate for retaining a hardenable composition according to claim 2 wherein each loop of yarn of one web overlaps each loop of yarn of the other web.

4. The substrate for retaining a hardenable composition according to claim 2 wherein said means interlocking each loop of yarn from one of said webs with each loop of yarn from the other of said webs includes directly knitting each loop of yarn from one web through each loop of yarn from the other web.

5. The substrate for retaining a hardenable composition according to claim 2 wherein said means interlocking each loop of yarn from one of said webs with each loop of yarn from the other of said webs includes indirectly interconnecting the respective loops of yarns of said webs through the use of additional yarns interposed therebetween.

6. A substrate for retaining a hardenable composition for use as an orthopedic support device, said hardenable composition being impregnated into said substrate in the form of a curing type resin, said substrate comprising a double layered knit fabric material having opposed front and back surfaces, said double layered fabric material having a first knitted fabric layer forming the front surface thereof and a second knitted fabric layer forming the back surface thereof, each of said first and second fabric layers being formed of yarns comprised of multiple fibers formed into loops, the loops of the respective fabric layers being located in overlaying relation to one another, each loop of yarn forming said first fabric layer being interconnected with at least one adjacent loop of yarn forming said second fabric layer, said curing type resin being impregnated into said yarns of said first and second fabric layers by capillary action along the fibers of said yarns.

7. The substrate for retaining a hardenable composition according to claim 6 wherein each loop of yarn forming said first fabric layer is disposed in overlaying relationship over more than one of the loops of yarns forming said second fabric layer.

8. The substrate for retaining a hardenable composition according to claim 6 wherein each loop of yarn forming said first fabric layer partly overlays two adjacent loops of yarns forming said second fabric layer.

9. The substrate for retaining a hardenable composition according to claim 6 wherein said curing type resin is a hydration type curing resin which is applied to said substrate in emulsion form and thereafter dried to allow only the solid component thereof to be retained on said substrate.

10. The substrate for retaining a hardenable composition according to claim 6 wherein said curing type resin is a thermoplastic type curing resin which is dissolved in an organic solvent and thereafter applied as a solution to said substrate.

11. The substrate for retaining a hardenable composition according to claim 6 wherein said curing type resin is a thermoplastic type curing resin which is heated until it becomes liquid in form, said thermoplastic type curing resin being applied to said substrate in liquid form and thereafter cooled to ambient temperature so as to be retained therein.

12. The substrate for retaining a hardenable composition according to claim 6 wherein said curing type resin is a water-curable type resin having low viscosity, said water-curable type resin being directly applied to said substrate.

13. The substrate for retaining a hardenable composition according to claim 6 wherein said curing type resin is a light-curable type resin having low viscosity, said light-curable type resin being directly applied to said substrate.

14. The substrate for retaining a hardenable composition according to claim 6 wherein said double layered knit fabric material is knitted such that a space is interposed between said first and second fabric layers, said first and second fabric layers being interconnected by a network of yarn extending through said space between said first and second layers.

15. The substrate for retaining a hardenable composition according to claim 14 wherein one of said first and second fabric layers is knitted into a plain pattern and the other of said first and second fabric layers is knitted into a mesh pattern.

16. A substrate having a curable resin material impregnated throughout particularly adaptable for use as an orthopedic support material, said substrate comprising a multi-layered material having front and back surfaces and including a pair of knitted fabric layers, one of said pair of knitted fabric layers forming the front surface of said multilayered material and one of said pair of knitted fabric layers forming the back surface of said multilayered material, each of said fabric layers including yarns of multiple non-glass fiber bundles forming a plurality of loops, the loops of one fabric layer overlaying the loops of the other fabric layer, said pair of knitted fabric layers having a space therebetween and being interconnected by a network of yarn extending through said space, said network of yarn interconnecting each respective loop of yarn of said one fabric layer with at least one loop of yarn of said other fabric layer, said curable resin material being impregnated throughout said substrate by capillary action along the fibers of the yarns of said fabric layers, the resin impregnated substrate forming a rigid, air permeable structure when said resin is allowed to harden.

17. The substrate having a curable resin material impregnated throughout according to claim 16 wherein one of said pair of fabric layers is knitted into a plain pattern and the other of said pair of fabric layers is knitted into a mesh pattern.

* * * * *